US00PP32427P2

(12) United States Plant Patent
Klemm et al.

(10) Patent No.: US PP32,427 P2
(45) Date of Patent: Nov. 3, 2020

(54) ***DIANTHUS* PLANT NAMED 'KLEDP19309'**

(50) Latin Name: *Dianthus caryophyllus*
Varietal Denomination: KLEDP19309

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,271

(22) Filed: Mar. 10, 2020

Related U.S. Application Data

(60) Provisional application No. 62/973,971, filed on Nov. 4, 2019.

(51) Int. Cl.
*A01H 6/30* (2018.01)
*A01H 5/02* (2018.01)

(52) U.S. Cl.
USPC ..... Plt./272

(58) Field of Classification Search
USPC ..... Plt./272
See application file for complete search history.

*Primary Examiner* — Annette H Para
(74) *Attorney, Agent, or Firm* — Barbara Campbell; Weatherly IP Solutions, LLC

(57) ABSTRACT

A new *Dianthus* plant designated 'KLEDP19309' particularly distinguished by dark red-purple single, round flowers and an upright habit, is disclosed.

1 Drawing Sheet

Genus and species: *Dianthus caryophyllus*.
Variety denominations: 'KLEDP19309'.

BACKGROUND OF THE NEW PLANT

The present invention comprises a new and distinct variety of *Dianthus*, botanically known as *Dianthus caryophyllus*, and hereinafter referred to by the variety name 'KLEDP19309'. 'KLEDP19309' originated from a cross from between the female *Dianthus* parent 'DSS-2014-1046' (unpatented) and the male *Dianthus* parent 'DCP-2001-TU 006' (unpatented) in The Netherlands in summer 2015.

In September 2016, 'KLEDP19309' was first vegetatively propagated by vegetative stem cuttings. 'KLEDP19309' was found to reproduce true to type in successive generations of asexual propagation in Stuttgart, Germany via vegetative stem cuttings.

SUMMARY

The following are the most outstanding and distinguishing characteristics of 'KLEDP19309' when grown under normal horticultural practices in Latina, Italy and Stuttgart, Germany.

1. Dark red-purple single, round flowers; and
2. An upright habit.

DESCRIPTION OF THE PHOTOGRAPH

This new *Dianthus* plant is illustrated by the accompanying photograph. The photograph shows the whole plant, including the flowers and foliage and buds. The colors shown are as true as can be reasonably obtained by conventional photographic procedures. The photo is of a 14-week-old plant of 'KLEDP19309'. The photo was taken in Stuttgart, Germany, indoors, in March 2017.

DESCRIPTION OF THE NEW VARIETY

The following detailed descriptions set forth the distinctive characteristics of 'KLEDP19309'. The data which define these characteristics were collected from asexual reproductions carried out in Latina, Italy. Data was collected in May 2019 on plants that were potted in week 389 of 2018. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP19309'.

Parentage:
- *Female parent*.—'DSS-2014-1046' (unpatented).
- *Male parent*.—'DCP-2001-TU 006' (unpatented).

Plant:
- *Propagation type*.—Vegetative stem cuttings.
- *Time to produce a rooted young plant*.—4 weeks.
- *Plant form*.—Upright.
- *Plant height*.—10.0 cm.
- *Plant diameter or spread*.—20.0 cm.
- *Rooting description*.—Fine, white, and habit is lanceolate-shaped.

Lateral branches:
- *Length*.—14.0 cm.
- *Diameter*.—0.2 cm.
- *Internode length*.—4.3 cm.
- *Node length*.—1.8 cm.
- *Node diameter*.—0.1 cm.
- *Texture*.—Smooth.
- *Color*.—RHS 137B (Green).

Foliage:
- *Arrangement*.—Opposite.
- *Length*.—5.5 cm.
- *Width*.—0.7 cm.
- *Shape*.—Lanceolate.
- *Apex*.—Acute.
- *Base*.—Obtuse.

*Margin*.—Entire.

*Texture* (*both upper and lower surfaces*).—Smooth.

*Immature leaf color*.—Upper surface: RHS N137B (Green). Lower surface: RHS N138B (Green).

*Mature leaf color*.—Upper surface: RHS 147A (Yellow-Green). Lower surface: RHS N137B (Green).

*Venation pattern*.—Parallel.

*Venation color* (*both upper and lower surfaces*).—RHS 144B (Yellow-Green).

Flowers:

*Flower type and habit*.—Round, single.

*Fragrance*.—Present, sweet.

*Natural flowering season*.—Spring to fall.

*Flower longevity on the plant*.—10 to 12 days.

*Buds*.—Length: 2.0 cm. Diameter: 0.5 cm. Shape: Elliptic. Color: RHS 144B (Yellow-Green) and RHS N77A (Purple).

*Corolla*.—Quantity of petals per flower: 5. Corolla height: 0.5 cm. Petal length: 2.2 cm. Petal width: 1.6 cm. Petal shape: Spoon-shaped. Petal apex: Obtuse. Petal base: Acute. Petal margin: Crenate. Petal texture (both upper and lower surfaces): Smooth. Petal color (both immature and mature): Upper surface: RHS 71A (Red-purple). Lower surface: RHS 72B (Red-Purple).

*Calyx*.—Quantity of sepals per flower: Composed of 6 sepals. Calyx height: 2.0 cm. Calyx diameter (at the apex): 0.8 cm. Sepal texture (both upper and lower surfaces): Smooth. Sepal color: Upper surface: RHS 137A (Green) with RHS N77A (Purple). Lower surface: RHS 145C (Yellow-Green).

Peduncles:

*Length*.—2.0 cm.

*Diameter*.—0.1 cm.

*Strength*.—Medium.

*Texture*.—Smooth.

*Color*.—RHS N138B (Green).

Reproductive organs:

*Stamens*.—Quantity per flower: 7. Filament length: 2.2 cm. Filament color: RHS 157A (Green-White). Anther length: 0.2 cm. Anther diameter: 0.1 cm. Anther color: RHS 72B (Red-Purple). Pollen amount: Absent.

*Pistils*.—Quantity per flower: 1. Pistil length: 2.0 cm. Style length: 1.5 cm. Style color: RHS NN155B (White). Stigma shape: Filamentous. Stigma color: RHS 72A (Red-Purple). Ovary size: 0.5 cm. Ovary shape: Oval. Ovary color: RHS 145B.

Fruit and seed set: Not observed.

Disease and pest/insect resistance: No disease and pest/insect resistance observed.

COMPARISON OF 'KLEDP19309' WITH PARENTAL LINES AND KNOWN VARIETY

'KLEDP19309' is distinguished from the parental lines as described in Table 1.

TABLE 1

Comparison with Parental Lines

| Characteristic | 'KLEDP19309' | Female Parent 'DSS-2014-1046' | Male Parent 'DCP-2001-TU 006' |
|---|---|---|---|
| Flower color | Dark-purple | Orange | Yellow red stripes |
| Earliness to flower | Very early | Early | Medium early |

'KLEDP19309' can be compared to the commercial *Dianthus* variety 'Beso' (unpatented). Differences between the varieties are described in Table 2.

TABLE 2

Comparison with Similar Variety

| Characteristic | 'KLEDP19309' | 'Beso' |
|---|---|---|
| Earliness to flower | Very early | Medium early |
| Vigor | Compact | Vigorous |

We claim:

1. A new and distinct variety of *Dianthus* plant designated 'KLEDP19309' as illustrated and described herein.

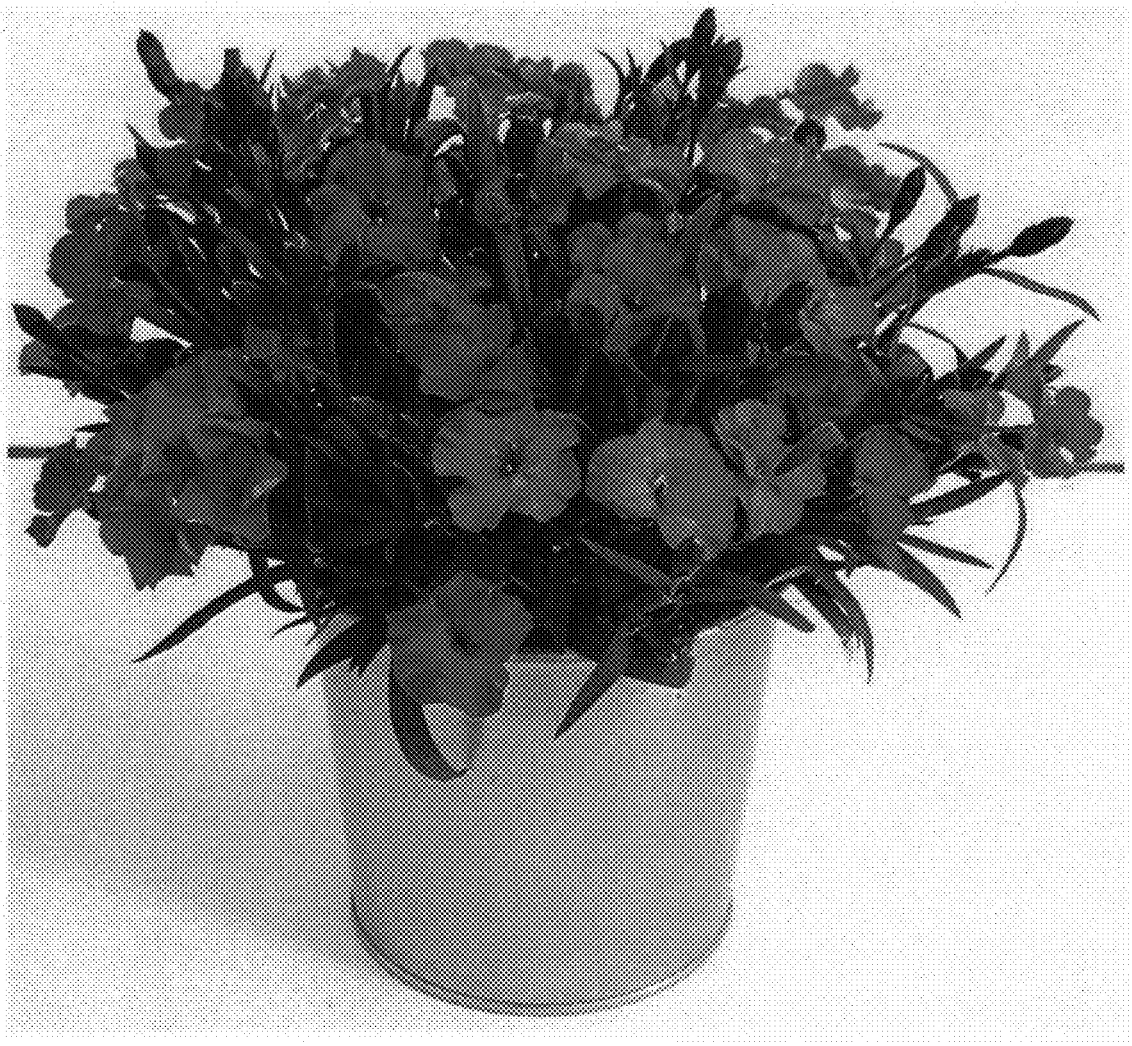

* * * * *